United States Patent [19]

Pavelka

[11] Patent Number: 4,582,508

[45] Date of Patent: Apr. 15, 1986

[54] GARMENT FOR RECEIVING CATHETERS AND THE LIKE

[76] Inventor: Wilma F. Pavelka, Rte. 1, Box 72-C, Marble Falls, Tex. 78654

[21] Appl. No.: 655,367

[22] Filed: Sep. 27, 1984

[51] Int. Cl.$^4$ .............................................. A61M 5/32
[52] U.S. Cl. ................................ 604/179; 2/DIG. 7; 128/DIG. 6
[58] Field of Search .............................. 604/179, 174; 128/DIG. 6; 2/DIG. 7

[56] References Cited

U.S. PATENT DOCUMENTS 4,087,864   5/1978   LaBove et al. .................. 604/174

FOREIGN PATENT DOCUMENTS

WO82/04399  12/1982  European Pat. Off. ............ 604/174
75753        4/1983  European Pat. Off. .......... 2/DIG. 7

Primary Examiner—Melvyn J. Andrews
Attorney, Agent, or Firm—George L. Williamson

[57] ABSTRACT

A garment is provided for holding, storing, supporting, and receiving certain indwelling catheters, e.g., a Hickman catheter or similar device to a patient's body. The garment is generally comprised of three elements including straps to hold said garment securely to patient's body and a pocket element within which to store said catheter. Fastening means are provided to connect the elements, said means being of various types. The garment is made of various types of material including disposable or throw away material.

27 Claims, 4 Drawing Figures

GARMENT FOR RECEIVING CATHETERS AND THE LIKE

BACKGROUND OF THE INVENTION

The present invention relates to a garment or strap-type device for holding and/or retaining certain indwelling catheters, e.g., a Hickman catheter, or similar device to a patient's body.

Garments and/or devices for holding or storing catheters or similar devices in various positions to patients' bodies have been described in the prior art. In U.S. Pat. No. 4,087,864, La Bove, et al., described a vest provided with pouches and pockets for holding items related to the use of intravenous medication. In U.S. Pat. No. 3,160,158, Rayhart, described a device for securing catheters adjacent to a patient's body.

In U.S. Pat. No. 3,878,849, Muller, et. al., described a therapeutic appliance for holding a tube alongside a patient's body. In U.S. Pat. No. 4,096,863, Kaplan, et. al., described a separable fastener in the form of a strap for holding medical tubes to a human body. In U.S. Pat. No. 3,895,629, Snyder, described a garment for holding a medical instrument in place within a body aperture.

However, none of the previously mentioned patents suggested a device for holding certain indwelling catheters, e.g., a Hickman catheter, or similar device to a patient's body. Therefore, it is an objective of the present invention to do so. A further objective of the present invention is to provide a garment which will allow for easy storage and use of certain indwelling catheters, e.g., a Hickman catheter or similar device. A further objective of the present invention is to protect the exposed end of the catheter by safely storing it near the patient's body and to allow the patient to move about freely with the catheter in place. An additional objective of the present invention is to safely secure a catheter to the body without using medical adhesive tape thereby avoiding the irritation to one's body and possible skin infection caused by prolonged use of said tape.

A Hickman indwelling catheter, consists of, generally speaking, a small rubber tube surgically implanted into the right atrium of the heart and is used to provide easy access to a patient's circulatory system. A typical schematic of a patient with a Hickman catheter or the like in operative connection is shown in FIGS. 1 and 2 of the drawings. A Hickman catheter is generally used for drawing blood, administering chemotherapy medications, and for giving blood products to the patient. However, the Hickman catheter does require daily care since it must be irrigated or flushed each day with a special solution. But even with this drawback, the Hickman catheter offers advantages to, e.g., cancer patients, who require frequent blood tests or chemotherapy in that it avoids frequent needle punctures, associated fears and anxiety and related risks of skin infections.

SUMMARY OF THE INVENTION

The present invention provides a new and improved garment for holding, supporting, receiving and storing certain indwelling catheters, e.g., a Hickman catheter or similar device, to a patient's body. The garment is comprised generally of three (3) elements: (1) a first strap-like element to wrap around the patient's body in the horizontal plane near the patient's waist-line; (2) a front pocket element within which to hold, support, receive and store the catheter; and (3) a second strap-like element to connect the first strap-like element to the front pocket by extending over the patient's shoulder so as to provide vertical support to the pocket element.

Accordingly, with the garment and catheter in place, the patient can move about freely with no fear of the catheter dangling free so as to be caught or snagged on an object. Furthermore, the catheter can be easily accessed for use or maintenance by the patient. Additionally, use of said garment greatly reduces risk of skin infection caused by prolonged use of medical tape.

DESCRIPTION OF THE PREFERRED EMBODIMENT(s)

Turning to the drawings, more particularly FIGS. 1, 2, 3, and 4, there is depicted the major elements of the invention. A first strap-like body attachment element, 11, being deposed more or less in the horizontal plane around or near the patient's waist, said strap-like element being used for securing the pocket, 12, for storing the indwelling catheter. Furthermore, a second strap-like body attachment element, 13, being more or less a shoulder strap or the like for connecting said first strap, 11, with the pouch, 12, by extending over the patient's shoulder to provide further support for the pocket, 12.

Figure 1:
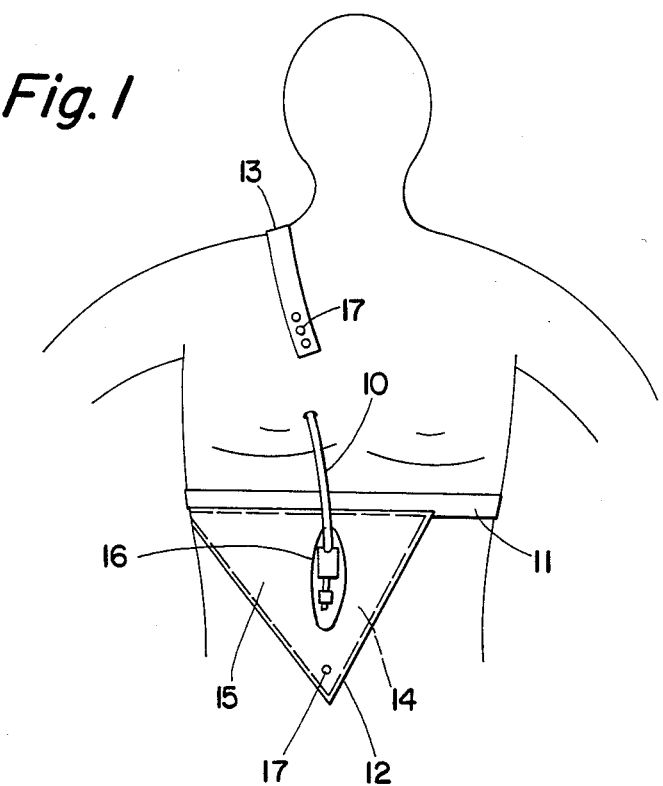
FIG. 1 is a front view of the invention shown in operative connection to patient's body.
Figure 2:
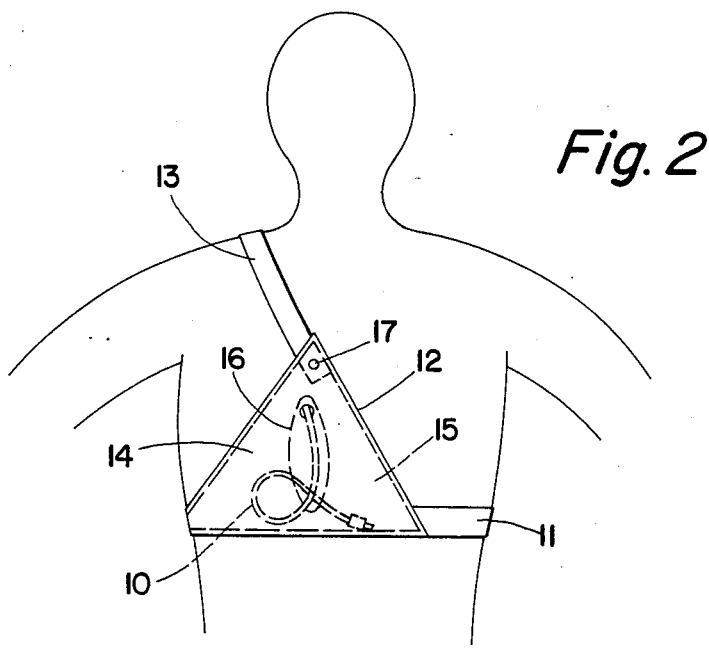
FIG. 2 is a front view of the invention shown in operative connection to the patient's body.

In FIGS. 1 and 2, the pocket, generally depicted at 12, is composed of two layers being a front outer layer of material, 14, and a rear, inner layer of material deposed next to the patient's body in FIG. 2, being more or less depicted at 15. Said two layers, 14 and 15, forming the inner and outer surfaces of the pocket wherein is stored the indwelling catheter as shown in operative connection in FIG. 2 said pocket being provided with an opening, 16, in the rear or inner layer of material, 15, through which the catheter or the like is inserted into the inner void or space of the pocket for storage. Said pocket, 12, could also be provided with an opening in the front or outer layer of material for insertion of said catheter.

The two layers of material, 14 and 15, comprising the front and rear layers of said pocket of the invention, can be attached to each other by sewing, stapling, gluing, pressing, snapping and/or otherwise formed into a, more or less, single pocket or pouch generally shown as 12. Furthermore, in FIGS. 1 and 2, there is exhibited a fastening means, 17, for attaching said shoulder strap, 13, to the pocket, 12, so as to provide support in the vertical plane to said pocket, 12. Said fastening means, 17, will be more thoroughly described later in this specification. The indwelling catheter generally depicted as 10, in FIG. 2, is shown in operative connection in FIG. 2 as being coiled and inserted in the space provided in the interior of the pouch generally shown as 12, being formed of said two layers 14 and 15. In FIG. 1, said fastening means, 17, is shown as actually having a plurality of said fastening means to allow one to adjust the garment to snugly fit one's body.

Figure 3:
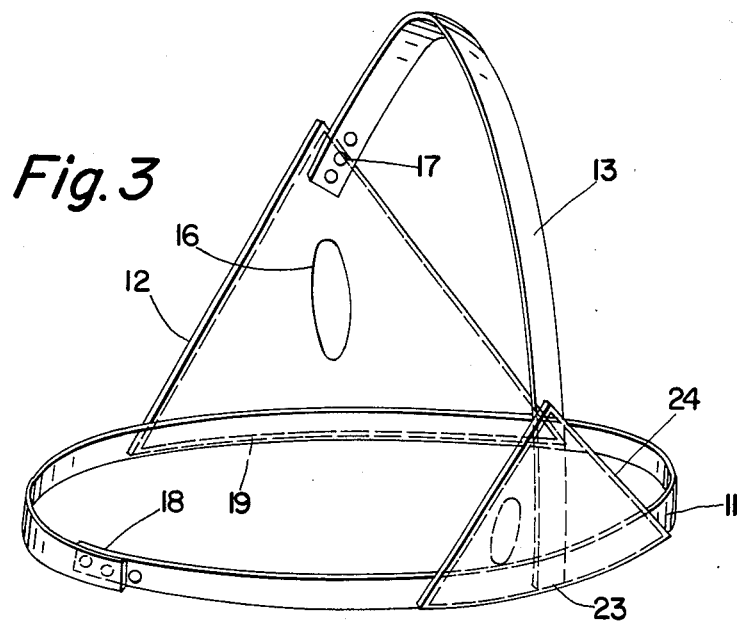
FIG. 3 is a rear perspective view of the invention.

In FIG. 3, there is shown fastening means, 17, at the point attaching the pouch, 12, to the shoulder strap, 13, and fastening means, 18, for connecting the two ends of said first waist strap, 11. Said fastening means, 18, being shown in the plurality to facilitate fitting the garment to one's body. Said fastening means, 17 and 18, will be more fully described in association with FIG. 4. In FIG. 3, the pouch generally shown as 12, is shown attached to the waist strap, 11, at the hidden line, 19. Said pouch, 12, could be attached to said waist strap, 11, along the line, 19, by sewing, stapling, pressing, gluing, snapping, buttoning, hooking, tying, and/or otherwise being attached so as to be connected therewith.

Figure 4:
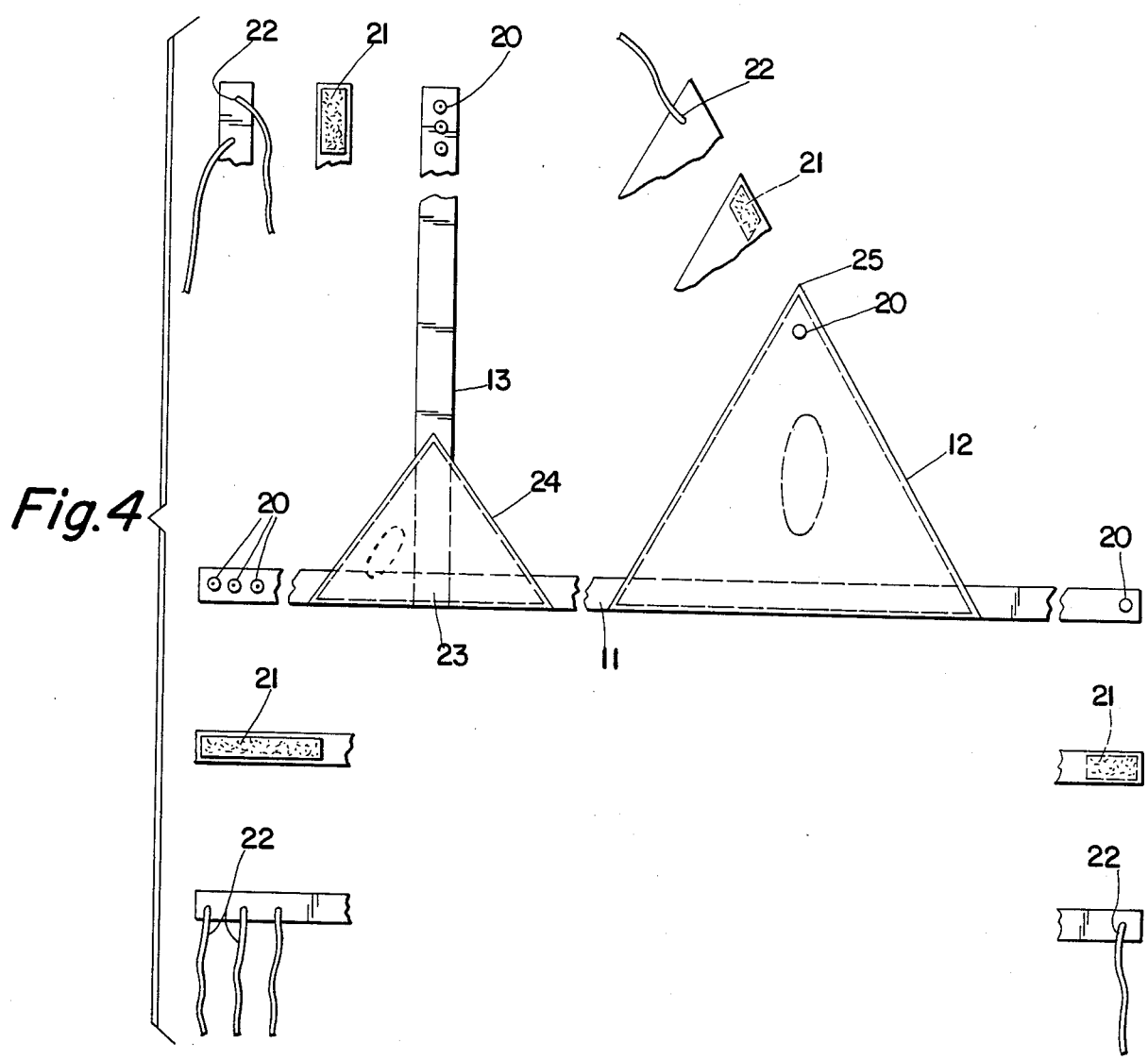
FIG. 4 is a front elevation view of the invention including partial views of fastening means.

In FIG. 4, said fastening means, 17, can be manufactured so as to consist of snaps, 20, velcro, 21, and/or strings, 22. Furthermore, in FIGS. 3 and 4, the connection between shoulder strap, 13, and waist strap, 11, is shown at 23. Straps, 13 and 11, could be attached at 23 by sewing, stapling, gluing, snapping, pressing and/or otherwise being connected together.

Other embodiments of the present invention are likely, e.g., the pocket, 12, could be situated to the opposing side of the patient's body shown in the illustrated embodiment or the garment could have multiple pockets as shown at 24 of FIGS. 3 and 4. Also, the pocket, 12, could be manufactured to have rounded corners as opposed to the pointed corners as illustrated in the drawings, said corners being depicted at 25 on FIG. 4.

It is obvious, from the foregoing teachings, that the invention can be easily and economically manufactured of various materials so as to provide a safe and convenient method of storing and receiving indwelling catheters, e.g., a Hickman catheter or the like. Furthermore, it is obvious from the foregoing teachings that the invention can be manufactured of many types of materials, including, but not limited to, cloth, plastics of various types, leather, rubber or the like, vinyls, and/or paper-type products, including paper products which would be more or less disposable in nature.

The teachings of this specification are meant to be illustrative and explanatory thereof and various changes in the size, shape and material as well as in the illustrative construction of the preferred embodiment may be made without departing from the spirit of the invention. It is obvious that many other embodiments of the invention could be easily manufactured by simply modifying the invention as hereinbefore described.

I claim:

1. A garment for a patient for holding, supporting, receiving and storing indwelling catheters, comprising:
    (a) a first body attachment element for mounting around a patient's body in the horizontal plane near the patient's waist;
    (b) a pocket element connected to said first body attachment element to hold, receive and store certain indwelling catheters;
    (c) a second body attachment element connecting in a second place said first body attachment element to said pocket element by extending over a patient's shoulder;
    (d) fastening means for connecting said elements;
    (e) said garment being of a size to receive and retain therein certain indwelling catheters about a human's body;
    (f) said pocket element having a rearside and inwardly deposed layer of material for being worn against the patient;
    (g) said pocket element further having a frontside and outwardly deposed layer of material being worn separated from the patient by said rearside and inwardly deposed layer of material; and
    (h) said rearside and inwardly deposed layer of material has an opening therein for insertion of said catheter.

2. The structure of claim 1, further comprising at least one additional pocket element mounted on said garment for receiving at least one indwelling catheter.

3. The structure of claim 1, wherein the corners of said pocket element are rounded.

4. The structure of claim 1, wherein the corners of said pocket element are pointed.

5. The structure of claim 1, wherein said pocket element is sewn to said first body attachment element and said first body attachment is sewn to said second body attachment element.

6. The structure of claim 1, wherein said pocket element is stapled to said first body attachment element and said first body attachment element is stapled to said second body attachment element.

7. The structure of claim 1, wherein said pocket element is glued to said first body attachment element and said first body attachment element is glued to said second body attachment element.

8. The structure of claim 1, wherein said pocket element snaps to said first body attachment element and said first body attachment element snaps to said second body attachment element.

9. The structure of claim 1, wherein said pocket element is attached to said first body attachment element and said first body attachment element is attached to said second body attachment element by artificial burr material.

10. The structure of claim 1, wherein said elements are one unbroken piece.

11. The structure of claim 1, wherein said two layers of material have been sewn.

12. The structure of claim 1, wherein said two layers of material have been stapled.

13. The structure of claim 1, wherein said two layers of material have been glued.

14. The structure of claim 1, wherein said two layers of material are one unbroken piece of material.

15. The structure of claim 1, wherein said elements are constructed of a cloth-like material.

16. The structure of claim 1, wherein said elements are constructed of a rubber-like material.

17. The structure of claim 1, wherein said elements are constructed of a paper-like material.

18. The structure of claim 1, wherein said elements are constructed of disposable material.

19. The structure of claim 1, wherein said fastening means are snaps.

20. The structure of claim 1, wherein said fastening means are artificial burr material.

21. The structure of claim 1, wherein said fastening means are strings consisting of the material of garment construction.

22. The structure of claim 1, wherein said pocket element and said second body attachment element, are for use and disposal to the right side of the patient's body.

23. The structure of claim 1, wherein said pocket element and said second body attachment element, are for use and disposal to the left side of the patient's body.

24. The structure of claim 1, wherein said pocket element is for use and disposal to the back side of the patient's body.

25. The structure of claim 1, further comprising resilient band means mounted with said first body attachment element and second body attachment element for use and conformation to the body of the patient.

26. The structure of claim 1, wherein said pocket element is detachably connected to said first body attachment element and second body attachment element.

27. The structure of claim 1, wherein said fastening means are a plurality so as to allow adjustment of the garment for snugly fitting a patient's body.

* * * * *